(12) United States Patent
Brugnoli et al.

(10) Patent No.: US 12,251,211 B2
(45) Date of Patent: Mar. 18, 2025

(54) DISPOSABLE COMBINED DEVICE WITH ANTIMICROBIAL FILTER AND FLOWMETER, FOR USE IN SPIROMETRY

(71) Applicant: COSMED S.r.l., Rome (IT)

(72) Inventors: Paolo Brugnoli, Pavona di Albano (IT); Simone Chiorboli, Pavona di Albano (IT)

(73) Assignee: COSMED S.R.L., Rome (IT)

( * ) Notice: Subject to any disclaimer, the term of this patent is extended or adjusted under 35 U.S.C. 154(b) by 801 days.

(21) Appl. No.: 17/393,906

(22) Filed: Aug. 4, 2021

(65) Prior Publication Data
US 2022/0039688 A1    Feb. 10, 2022

(30) Foreign Application Priority Data

Aug. 5, 2020 (EP) .................................... 20189563

(51) Int. Cl.
*A61B 5/087* (2006.01)
*B01D 46/00* (2022.01)
*B01D 46/54* (2006.01)

(52) U.S. Cl.
CPC .......... *A61B 5/087* (2013.01); *B01D 46/0028* (2013.01); *B01D 46/543* (2013.01); *A61B 2560/0285* (2013.01)

(58) Field of Classification Search
CPC ............ A61B 5/087; A61B 2560/0285; A61B 2562/18; A61B 5/0876; A61B 5/097; B01D 46/0028; B01D 46/543
See application file for complete search history.

(56) References Cited

U.S. PATENT DOCUMENTS

| | | | | |
|---|---|---|---|---|
| 4,083,245 A | * | 4/1978 | Osborn | A61B 5/08 73/861.53 |
| 4,993,269 A | * | 2/1991 | Guillaume | G01F 1/36 73/861.53 |

(Continued)

FOREIGN PATENT DOCUMENTS

EP          0331773           9/1989

OTHER PUBLICATIONS

Search Report for EP20189563, dated Dec. 16, 2020, 3 pages.

(Continued)

*Primary Examiner* — Andrey Shostak
(74) *Attorney, Agent, or Firm* — NIXON & VANDERHYE

(57) ABSTRACT

An entirely disposable combined antimicrobial filter and flowmeter device for spirometry applications comprises a tubular body, with an inlet end portion, an outlet end portion, and an intermediate portion of enlarged diameter in the form of a discoidal shell. In the discoidal shell both an antimicrobial filtering membrane and a discoidal net of plastic material generating a pressure differential are arranged, it has an outer peripheral edge fixed to an inner annular lip of one of said bell-shaped portions of the discoidal shell, said annular lip being coaxial to said cylindrical wall. One of the filtering membrane and the pressure differential generating network has an outer peripheral edge fixed to the cylindrical wall of the discoidal shell, while the other of the filtering membrane and the pressure differential generating network has an outer peripheral edge fixed to an inner annular lip of one of the bell-shaped portions defining the discoidal shell.

8 Claims, 7 Drawing Sheets

(56) References Cited

U.S. PATENT DOCUMENTS

Figure 1:
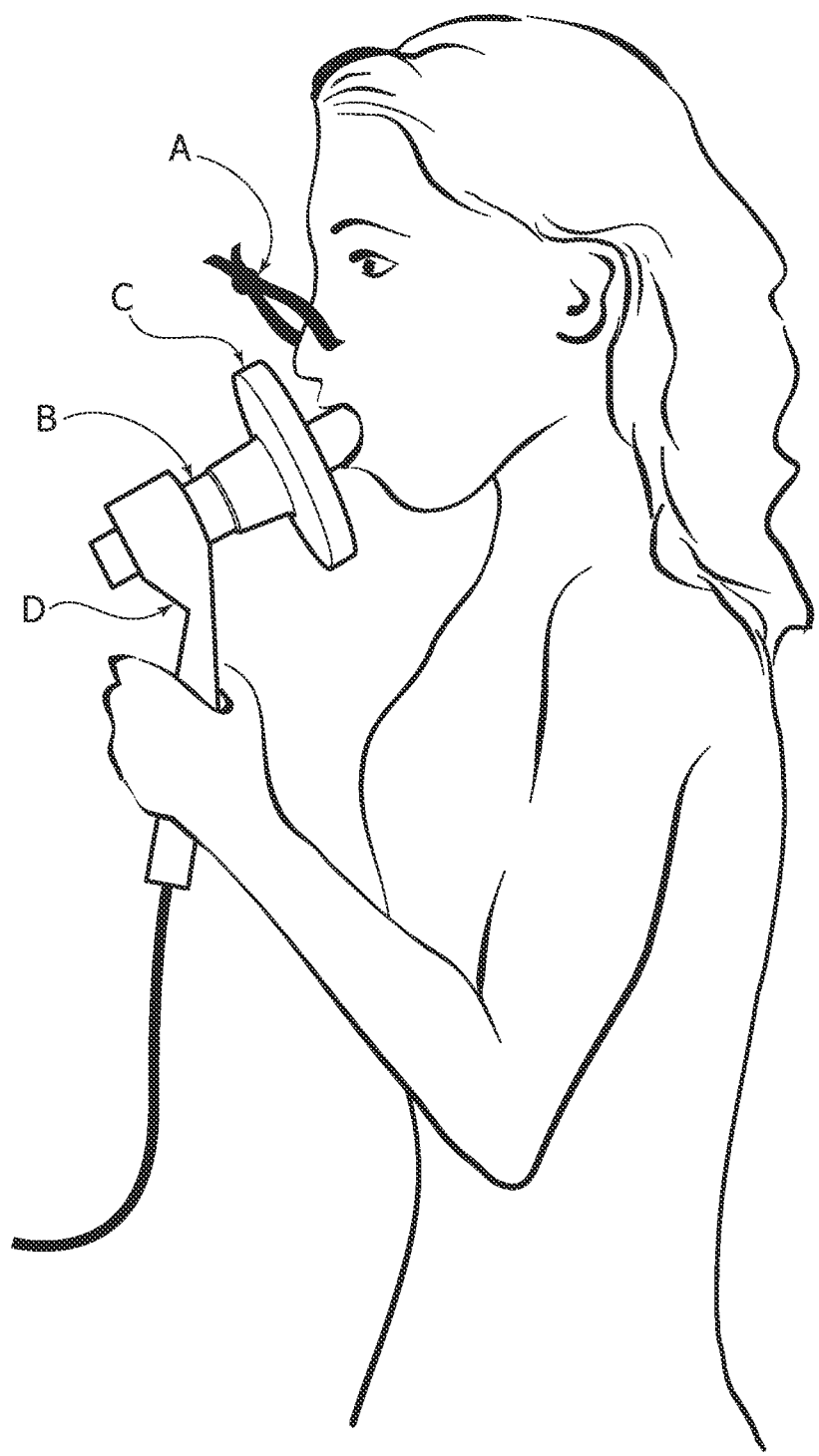

| | | | | |
|---|---|---|---|---|
| 5,230,727 | A * | 7/1993 | Pound | B01D 46/0012 |
| | | | | 55/494 |
| 6,090,049 | A * | 7/2000 | Cha | A61B 1/00142 |
| | | | | 600/538 |
| 2003/0120169 | A1* | 6/2003 | Jones | G01F 1/363 |
| | | | | 600/538 |
| 2017/0268980 | A1* | 9/2017 | Clayton | G01N 21/53 |
| 2018/0356266 | A1* | 12/2018 | Robbins | G01N 21/39 |

OTHER PUBLICATIONS

Graham et al., "Standardization of Spirometry 2019 Update. An official American Thoracic Society and European Respiratory Society Technical Statement," American Journal of Respiratory and Critical Care Medicine, vol. 200, No. 8, Oct. 15, 2019, 19 pp. e70-e88.

Clausen, "Lung volume equipment and infection control", European Respiratory Journal 1997, vol. 10, pp. 1928-1932.

Fleiseh, Der Pneumotachograph; ein Apparat zur Geschwindigkeitsregistrierung der Atemluftl), Aus dem Physiologischen Institut Zurich, Jul. 6, 1925, 10 pages.

* cited by examiner

DISPOSABLE COMBINED DEVICE WITH ANTIMICROBIAL FILTER AND FLOWMETER, FOR USE IN SPIROMETRY

This application claims priority to EP Patent Application No. 20 189 563.8 filed 5 Aug. 2020, the entire contents which is hereby incorporated by reference.

FIELD OF THE INVENTION

The present invention relates to a combined antimicrobial filter and flowmeter device, entirely disposable, for spirometry applications.

PRIOR ART

Spirometry is the assessment of a person's respiratory function, which can be carried out in a clinical (pulmonology), sports (for example, for evaluating fitness to practice sports) or legal (for example, in occupational medicine) context.

In particular, the evaluation tests consist of measuring the flow of exhaled/inhaled air through a flowmeter connected to the subject's mouth during particular maneuvers indicated by a specialized operator.

There are several types of flowmeters. The most common are the so-called Fleisch's pneumotachograph, Lilly's pneumotachograph, Pitot's pneumotachograph, the variable orifice flowmeter, the mass flowmeter, the turbine flowmeter and the ultrasonic flowmeter.

In the first four types of flowmeter, the flow of exhaled or inhaled air passes through a duct inside which there is a member that generates a pressure drop, which is a difference in pressure between the environments upstream and downstream of this member. This pressure drop is detected by two pressure sensors (or by a single differential pressure transducer) thanks to two holes placed on the sides of the member that generates this loss.

Spirometry is an established technique in medicine. Regarding the requirements of the necessary equipment, international standardization guidelines are available, among which the following can be mentioned:

*Standardization of Spirometry* 2019 *Update. An official American Thoracic Society and European Respiratory Society Technical Statement. Am J Respir Crit Care Med.* 2019, 200(8):e70-e88;

ERS/ATS 1997: *"Lung volume equipment and infection control"; European Respiratory Journal* 1997, 10: 1928-1932.

One of the important requirements to be respected is the adoption of solutions that ensure the protection of the user's airways from contact with viruses and bacteria that may be present in the environment or in the equipment.

There are currently substantially three methods to reduce the risk of cross-contamination between different users:

1) use of instrumentation in which all elements in contact with the exhaled and inhaled air by the user are disposable (disposable flowmeter);
2) interposition of an antimicrobial filter between the flowmeter (reusable) and the user's mouth;
3) use of a disposable cardboard mouthpiece and disinfection of the reusable flowmeter after each test (method almost completely abandoned).

Due to the recent COVID-19 pandemic, numerous scientific societies, including the European Respiratory Society, have recommended the adoption of additional precautions to protect not only the user subjected to the test, but also the surrounding environment and the health workers exposed to exhaled particles during respiratory function tests. This can be read in the following bibliographical reference:

Recommendation from ERS Group 9.1 (Respiratory function technologists/Scientists) Lung function testing during COVID-19 pandemic and beyond, available at the following link: ers.app.box.com/s/zsluu88wy51monroewd990itoz4tsn2h In fact, the respiratory function tests can envisage forced exhalations by the user with consequent generation of aerosol droplets, which could act as vectors of any viruses and/or bacteria, thus increasing the risk of infecting healthcare workers present in the environment.

In view of these needs, among the methods of preventing bacterial and/or viral contamination mentioned above, the most suitable is the use of an antibacterial and/or antiviral filter.

In the standardization guidelines for the use of antibacterial and/or antiviral filters, the following requirements are required:

the expiratory resistance of the assembly consisting of flowmeter and filter must not exceed the limit of 1.5 cm $H_2O$/l/sec up to flows of 14 l/sec, in order to ensure that the results are not altered;

the connection between the filter and the flowmeter must be completely sealed, so that all the air exhaled by the user is actually measured;

the volume of the assembly consisting of filter and flowmeter (dead space) must be as small as possible;

the operation of the filter barrier against the passage of viruses and bacteria must be adequate and demonstrated by independent tests.

FIG. 1 of the attached drawings shows the use of a flowmeter connected to an antiviral and/or antibacterial filter according to the prior art. In particular, the patient wears a nose clip A to close the nostrils, in order to convey all the exhaled air into a flowmeter B equipped with a handle D. An antibacterial and/or antiviral filter C is interposed between the flowmeter B and the patient's mouth, of the disposable type, intended to avoid contamination during the inhalation step.

Although systems similar to that shown in FIG. 1 do function, there are some problems associated with the use of an instrument of this type that may negatively affect the reliability of the measures and patient safety.

In particular, the response of any flowmeter may vary significantly depending on the antimicrobial filter connected thereto (the geometry of the filter affects the characteristics of the airflow, with the generation of any turbulence).

Furthermore, the quality of the antimicrobial filters offered by the market is often poor, so there is a risk of using filters with a reduced filtering power or that have undergone inadequate quality control processes, which do not guarantee the declared performance.

In addition to this, connection sometimes occurs of an antimicrobial filter on a flowmeter with an incompatible diameter by means of adapter fittings. This involves a probable introduction of unwanted leaks and/or an increase in the dead space of the measurement system, i.e. the volume of exhaled air that the patient is forced to breathe again, so often the aerodynamic characteristics provided by the assembly are altered. This causes a reduction in the accuracy of the measurements made.

Finally, the use of reusable flowmeters, even if protected by antibacterial and/or antiviral filters, implies that these flowmeters must be disinfected periodically, for example, once a day, and in any case on the outer surface every time it comes into contact with a user undergoing the test.

Figure 10:
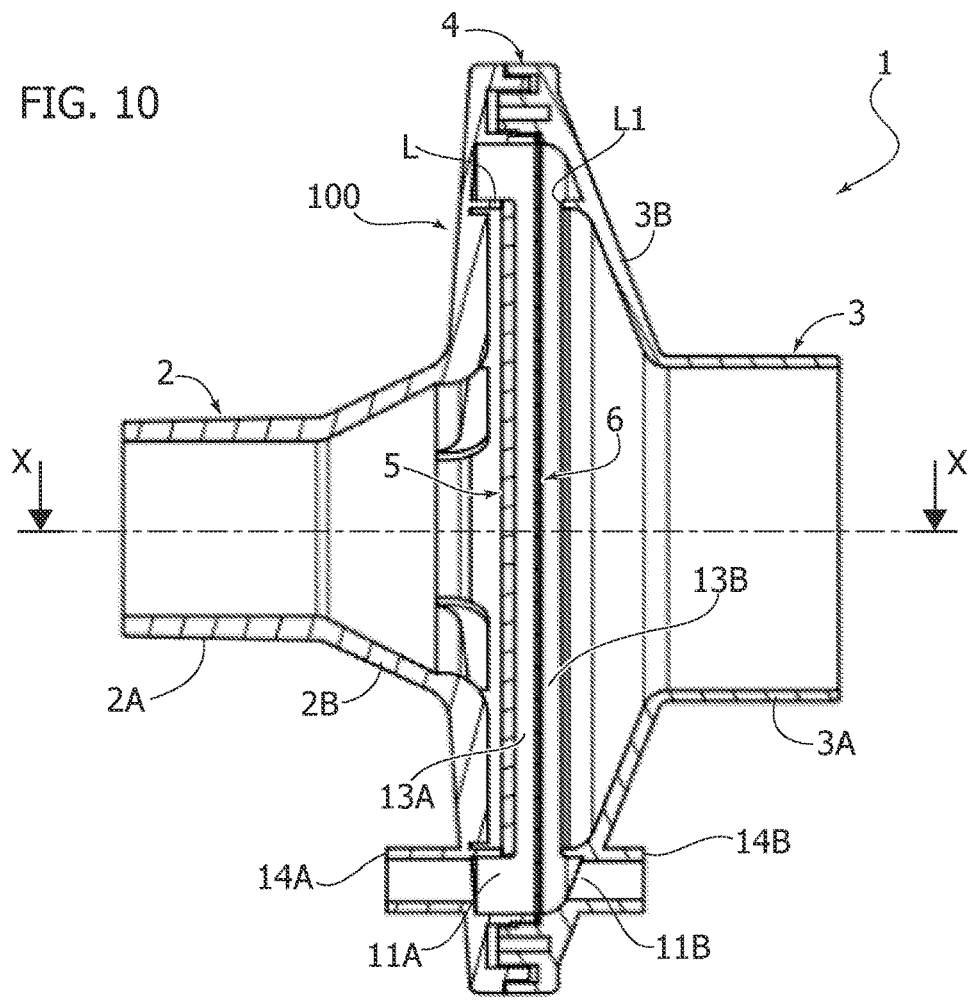

A device integrating an antimicrobial filter and a flowmeter, having the characteristics indicated in the preamble of claim 1, is illustrated in FIG. 10 US 20030120169 A1. The two outlets of the device that communicate with the chambers upstream and downstream of the pressure differential generator member are intended to be placed in communication with a measuring instrument, which measures the flow rate of the airflow that passes through the device according to a measurement of said pressure differential. This known solution involves the use of a face mask, as it is intended for measuring resting metabolism (calorimeter). It would not be suitable for performing respiratory function tests, wherein significantly higher respiratory flows (14 L/s) are reached. In any case, the problem in a solution of this type is that of allowing an adequate filtering capacity without generating excessive resistance to the flow. To obtain this result, the filtering membrane must have a considerably greater extension with respect to the section of passage of the airflow at the end portion, which is engaged by the patient's mouth. At the same time it is necessary that the total volume of the inner cavity of the device does not exceed a maximum limit.

For these reasons, the optimal configuration for a device of the type under discussion is that wherein the aforesaid intermediate portion of enlarged diameter is in the form of a discoidal shell, with an outer peripheral edge connected to the two end portions of the device by two strongly tapered portions, bell-shaped. A device of this type is known from U.S. Pat. No. 5,230,727 A1. However, in this device, the pressure differential generator member is constituted by a cylindrical plug of corrugated metal (according to the prior art by Fleisch A., "*Der Pneumotachograph; ein Apparat zur Geschwindigkeitsregistrierung der Atemluft.*", *Pflügers Archiv Eur J Physiol* 1925; 209: 713-22.) inserted into the outlet portion (with respect to exhalation flow) of the device. This solution is, therefore, not suitable for a disposable device.

OBJECT OF THE INVENTION

The object of the present invention is to overcome the drawbacks of the prior art.

In particular, an object of the present invention is to provide a combined disposable device, integrating an antimicrobial filter and a flowmeter, which is simple and economical, so as to be suitable for a single use, and which at the same time satisfies the needs of reduced overall resistance to the airflow, to prevent the patient's natural respiratory activity from being hindered, adequate protection from cross-contamination, reduced dead space of the system, intended as the volume of the space not occupied by the filter element and by the element generating the pressure differential, which is important to allow easy use by the patient, to avoid turbulence of the flow within the device, and to allow accurate measurements accordingly.

Another particular object of the invention is to use a pressure differential generator member configured in such a way that the pressure differential varies substantially linearly with the flow rate of the air flowing through the device, so as to make the flow measurement simple and reliable.

An additional object of the present invention is to produce a device of the type indicated above, capable of adequately protecting both the user subjected to spirometry analysis, the surrounding environment and the healthcare worker in charge of overseeing the analysis from microbial contamination.

SUMMARY OF THE INVENTION

In order to achieve one or more of the aforesaid objects, the invention relates to a combined disposable device integrating an antimicrobial filter and a flowmeter, for use in spirometry, said device comprising:

a tubular body, defining a cavity for the passage of an airflow, and having an inlet end portion, for engaging the mouth of a user, an opposite outlet end portion, substantially coaxial with the inlet portion, and an intermediate cylindrical portion, having an enlarged diameter with respect to the inlet portion and the outlet portion, a filtering membrane, arranged inside said intermediate portion of enlarged diameter, in such a way as to filter the entire airflow that passes through said tubular body, and a pressure differential generator member, in the form of a membrane parallel to and spaced apart from said filtering membrane, inside said intermediate portion of enlarged diameter, said pressure differential generator member being configured in such a way as to generate a pressure differential, in the entire airflow that passes through said tubular body, between an upstream side and a downstream side of said pressure differential generator member, with reference to the direction of the airflow, and two outlets defined by said tubular body and communicating, respectively, with two chambers defined in the cavity of said tubular body, respectively, upstream and downstream of said pressure differential generator member, said device being characterized in that:

said intermediate portion of enlarged diameter is in the form of a discoidal shell comprising an outer cylindrical wall and two opposed bell-shaped portions, connecting the outer cylindrical wall, respectively, with the two inlet and outlet end portions of said tubular body, said membrane defining said pressure differential generator member is in the form of a discoidal network of plastic material, and is located, together with said filtering membrane, inside said discoidal shell of enlarged diameter, one of said filtering membrane and said pressure differential generating network has an outer peripheral edge fixed to said cylindrical wall of the discoidal shell, while the other of said filtering membrane and said pressure differential generating network has an outer peripheral edge fixed to an inner annular lip of one of said bell-shaped portions of the discoidal shell, said annular lip being coaxial to said cylindrical wall.

The predisposition, as a pressure differential generator member, of a network of plastic material, inserted into the enlarged discoidal portion in which the filtering membrane is also inserted, allows obtainment of an adequate but not excessive resistance to flow, and a simple and reliable detection to be made possible, due to the fact that the pressure differential generated by the network varies substantially linearly as the flow varies. Furthermore, the overall volume of the inner cavity of the device is reduced to a minimum. Consequently, the flow of inhaled/exhaled air by the user makes a relatively short path, and the risk of unwanted air leaks occurring, which could negatively affect the reliability of the measurement, is substantially eliminated. In addition to this, the dead space, i.e. the volume of air that remains trapped in the device, and which is consequently breathed in again by the user during the analysis, is also significantly reduced, which makes the device easy to use for the patient. This also allows reduction or complete avoidance of turbulence in the airflow inside the device, and consequently increases the accuracy of the measurements made.

According to a further preferred characteristic, the plastic material network is configured to have an air permeability between 3000 liters/second m$^2$ and 6600 liters/second m$^2$.

According to a further preferred characteristic, the aforesaid tubular body comprises:
 a first element of plastic material comprising, in one piece, said inlet end portion and one of said bell-shaped portions, and
 a second element of plastic material comprising, in one piece, said outlet end portion and the other of said bell-shaped portions.

In one embodiment, the first element of plastic material and the second element of plastic material have radially outer edges directly connected to each other, so as to define said cylindrical wall, one of said filtering membrane and said generating network of a pressure differential having its outer peripheral edge clamped between said radially outer edges of the first and second elements of plastic material.

In a first example, the pressure differential generating network has its outer peripheral edge clamped between the radially outer edges of the first and second elements of plastic material. Furthermore, in this example, the filtering membrane has its outer peripheral edge fixed to the aforesaid inner annular lip, which is formed in the bell-shaped portion of said first element of plastic material that comprises the inlet portion of the device. Again in this example, one of the two aforesaid outlet passages is obtained in the bell-shaped portion of said first element of plastic material, which comprises the inlet portion of the device, and communicates with a chamber defined between the filtering membrane and the pressure differential generating network, while the other of said outlet passages is formed in the bell-shaped portion of said second element of plastic material, which comprises the outlet portion of the device and communicates with a chamber located downstream of the pressure differential generation network.

In another example, the filtering membrane has its peripheral outer edge clamped between said radially outer edges of the first and second elements of plastic material. In this example, the pressure differential generating network has its outer peripheral edge fixed to said inner annular lip, which is formed in the bell-shaped portion of said second element of plastic material, which comprises the outlet portion of the device. Again in this example, both of the aforesaid outlet passages are formed in the bell-shaped portion of said second element of plastic material, which comprises the outlet portion of the device. An outlet passage communicates with a chamber defined between the filtering membrane and the pressure differential generating network, the other outlet passage communicates with a chamber located downstream of the pressure differential generation network.

In another embodiment, the body of the device comprises at least one annular element of plastic material interposed between the radially outer edges of said first and second elements of plastic material.

DETAILED DESCRIPTION OF THE INVENTION

Figure 2:
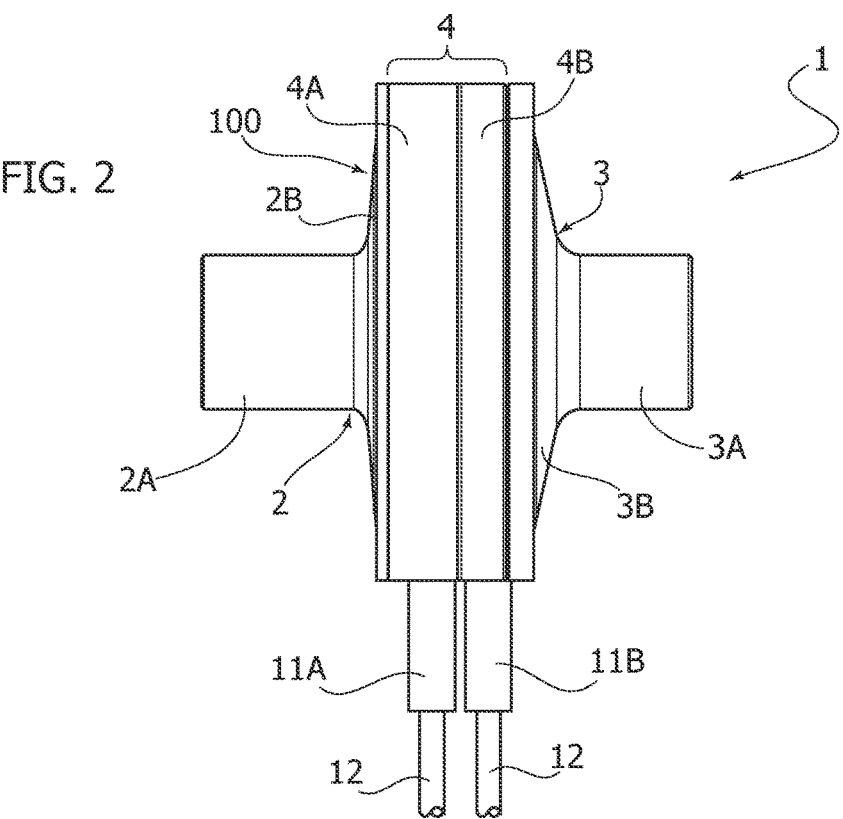
Figure 3:
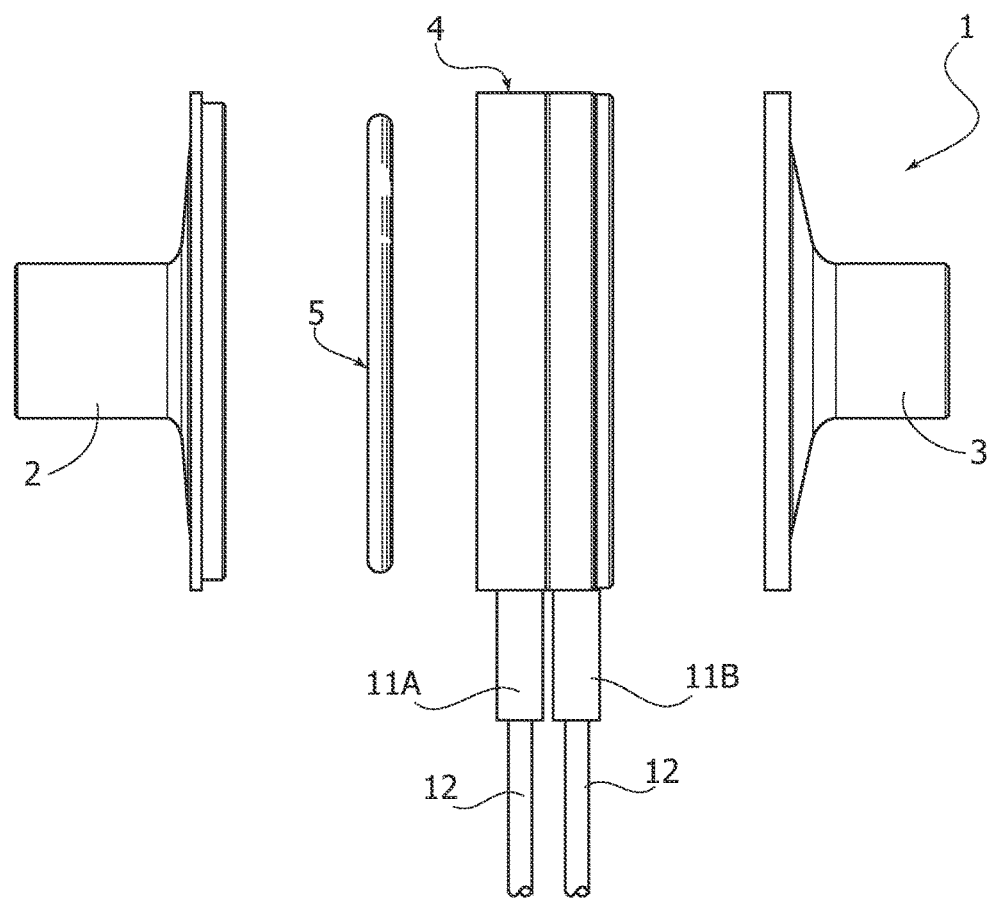
Figure 4:
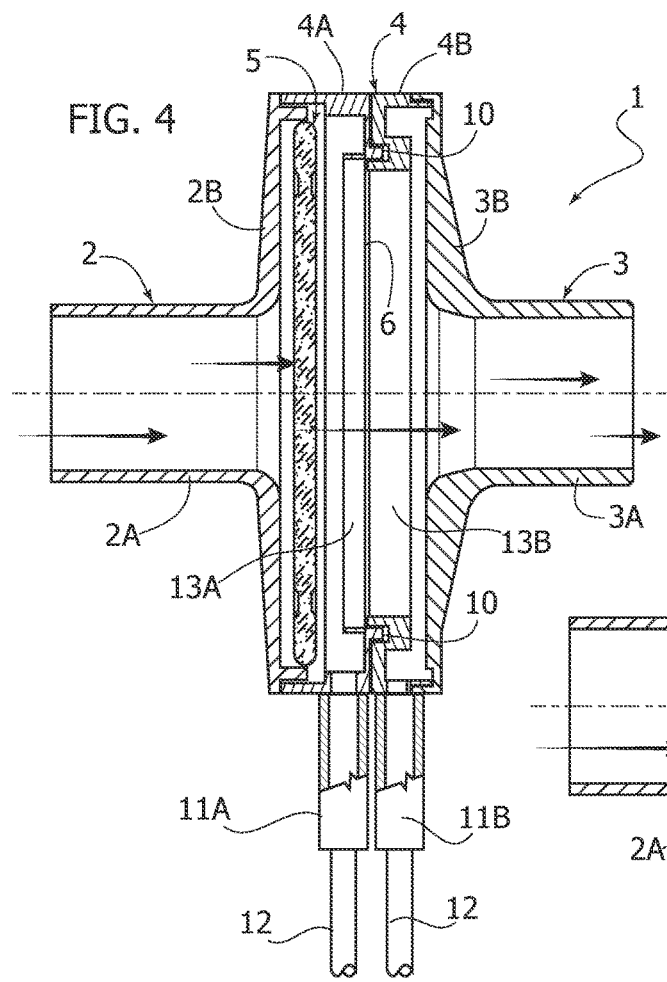
Figure 5:
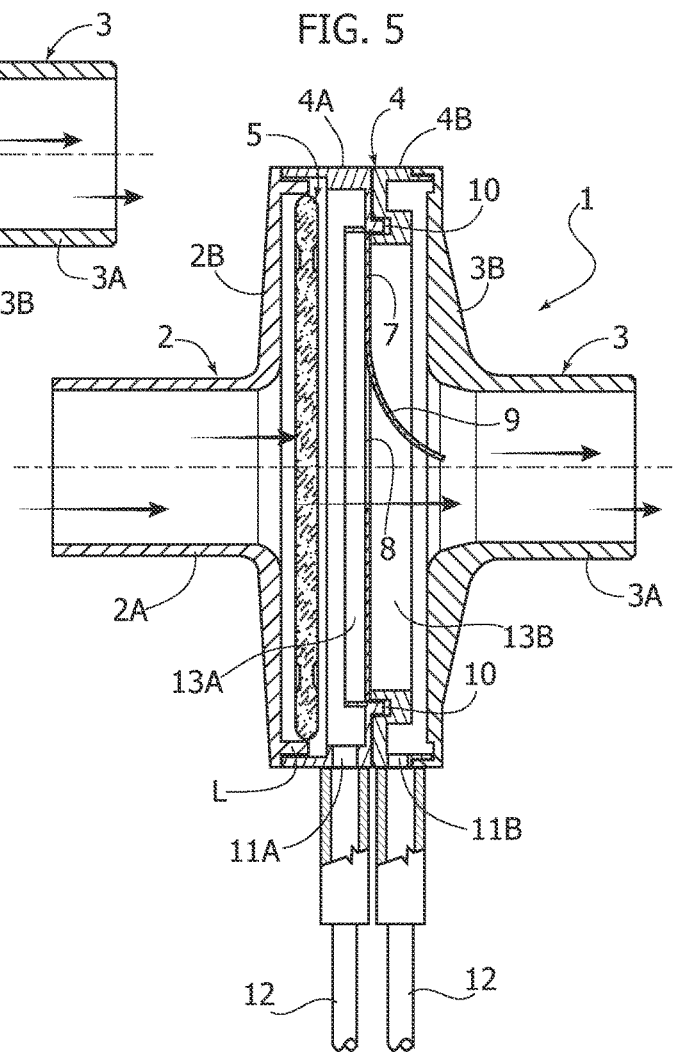
Figure 6A:
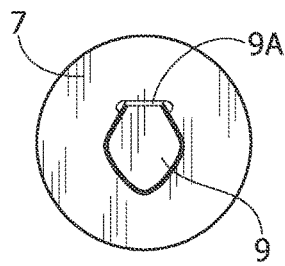
Figure 6B:
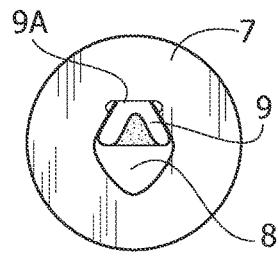
Figure 7:
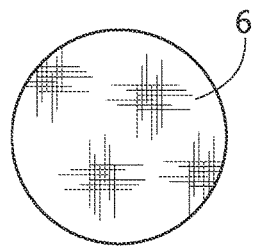
Figure 8:
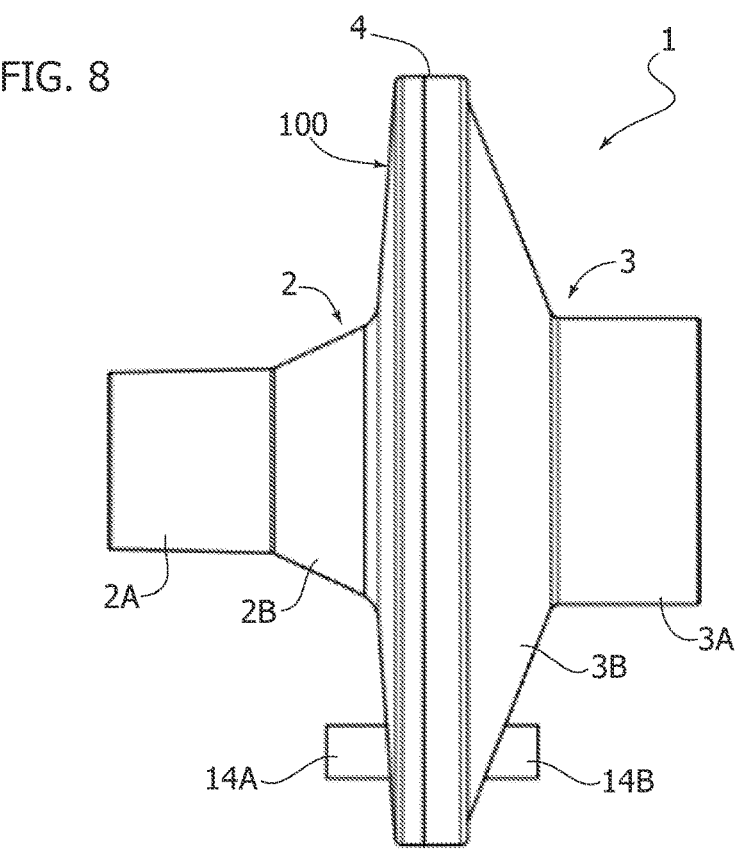
Figure 9:
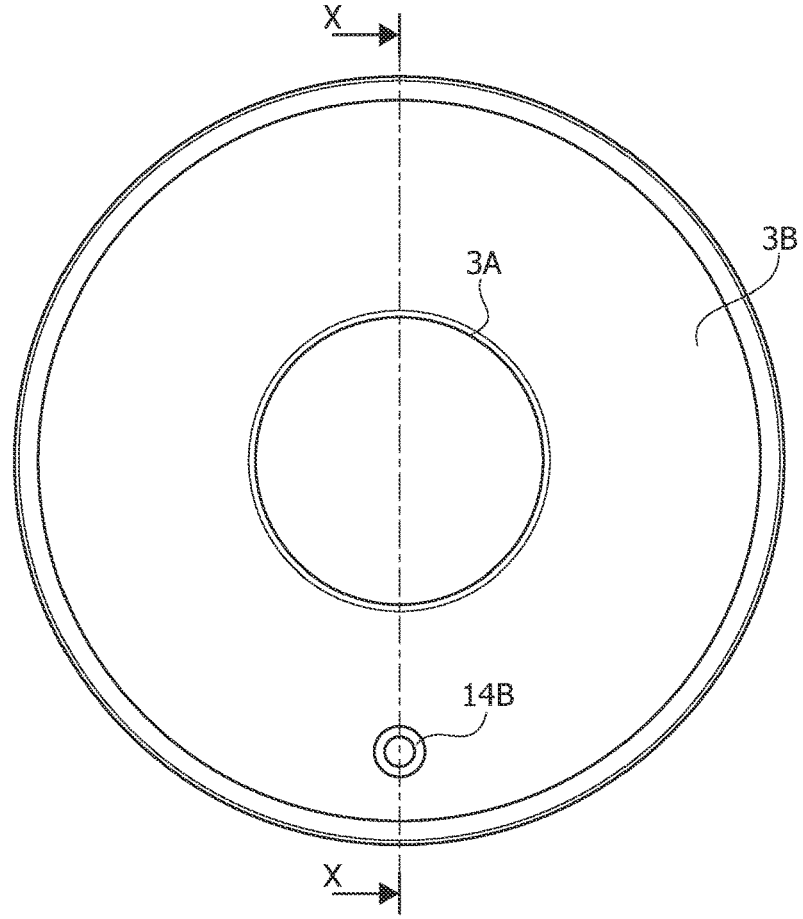
Figure 11:
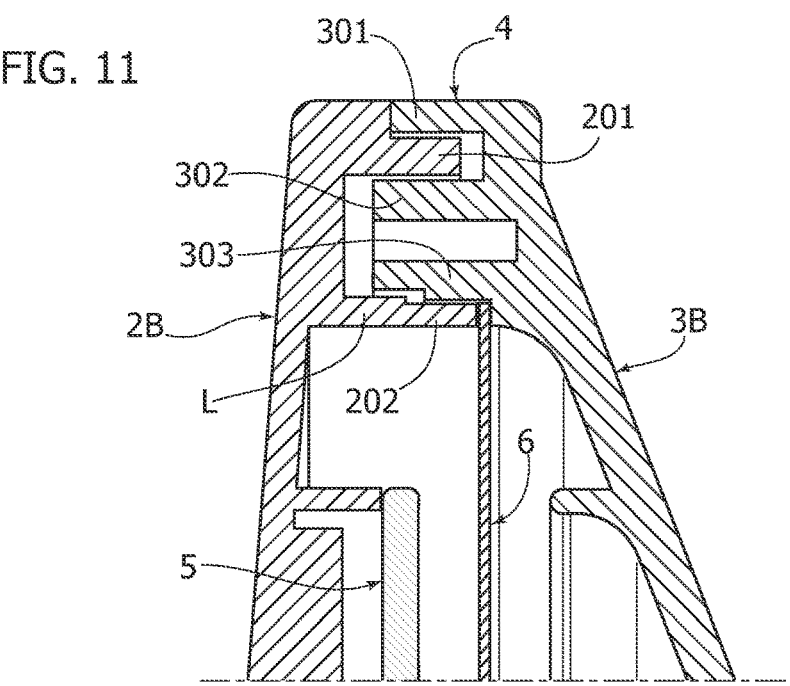
Figure 12:
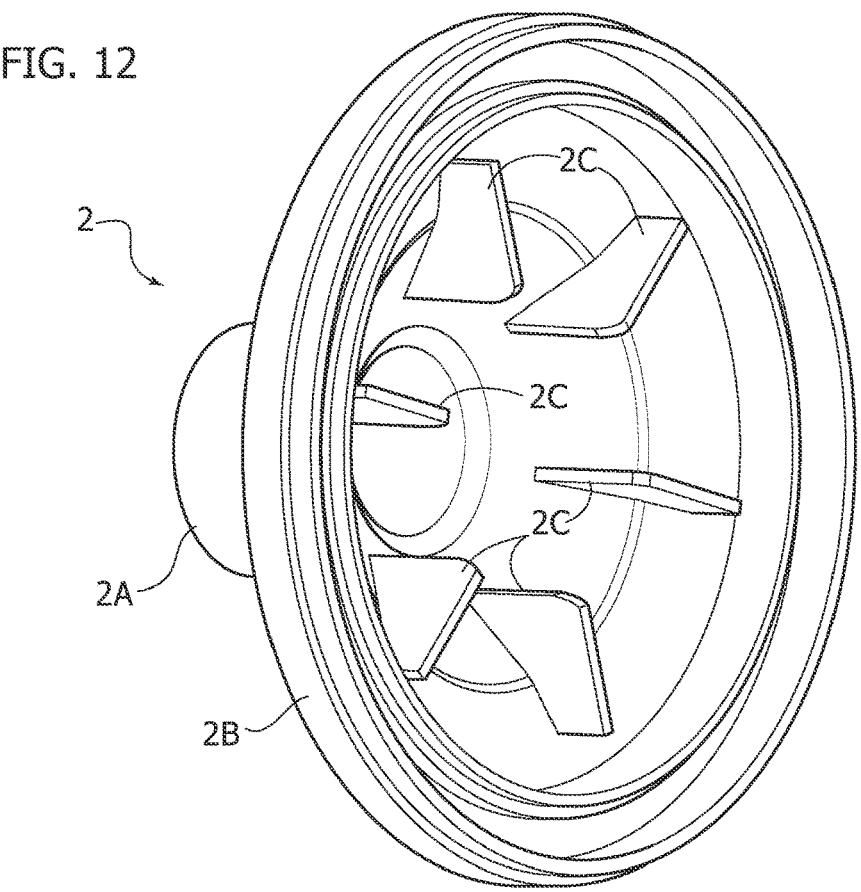
Figure 13:
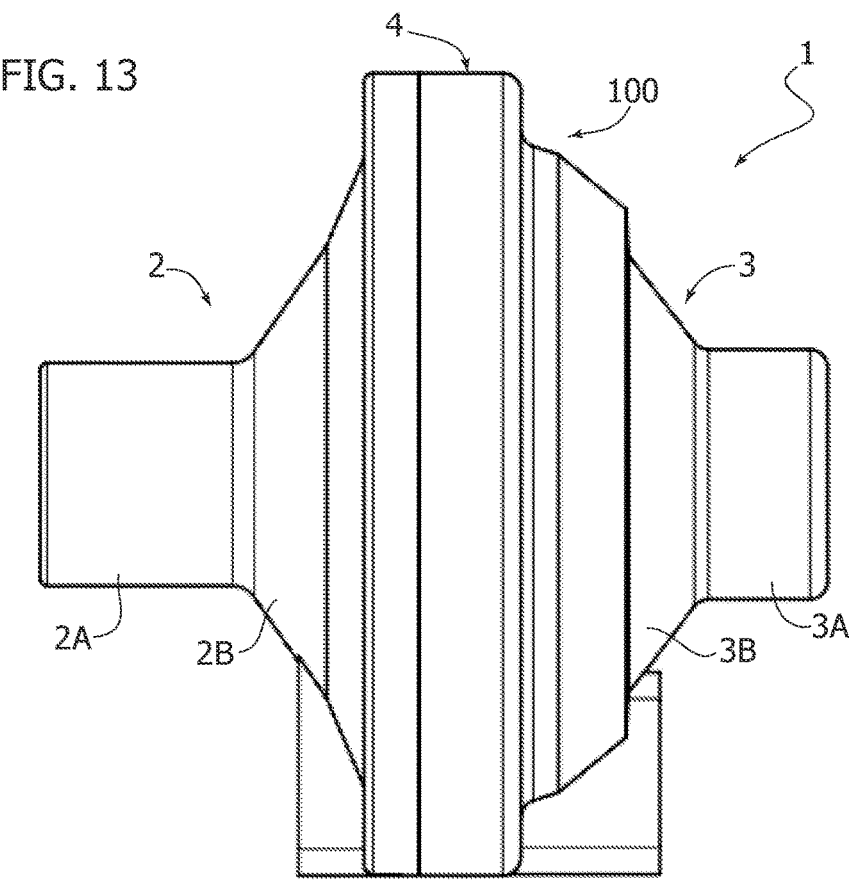
Figure 14:
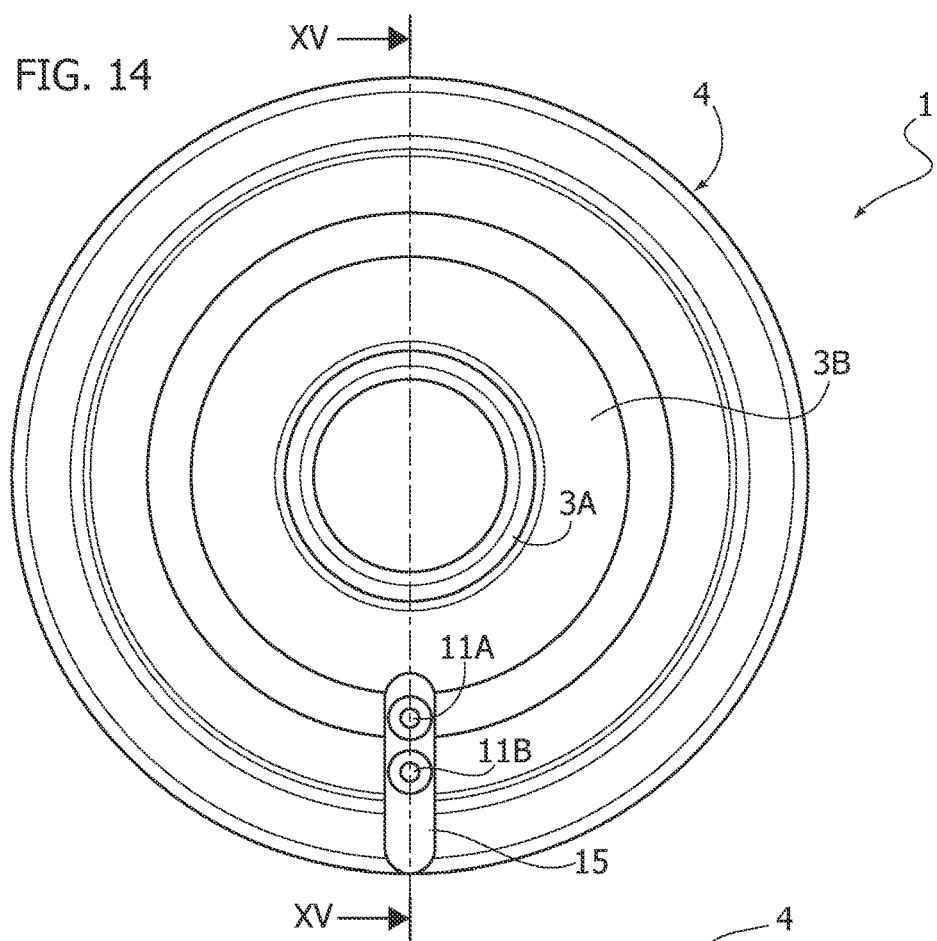
Figure 15:
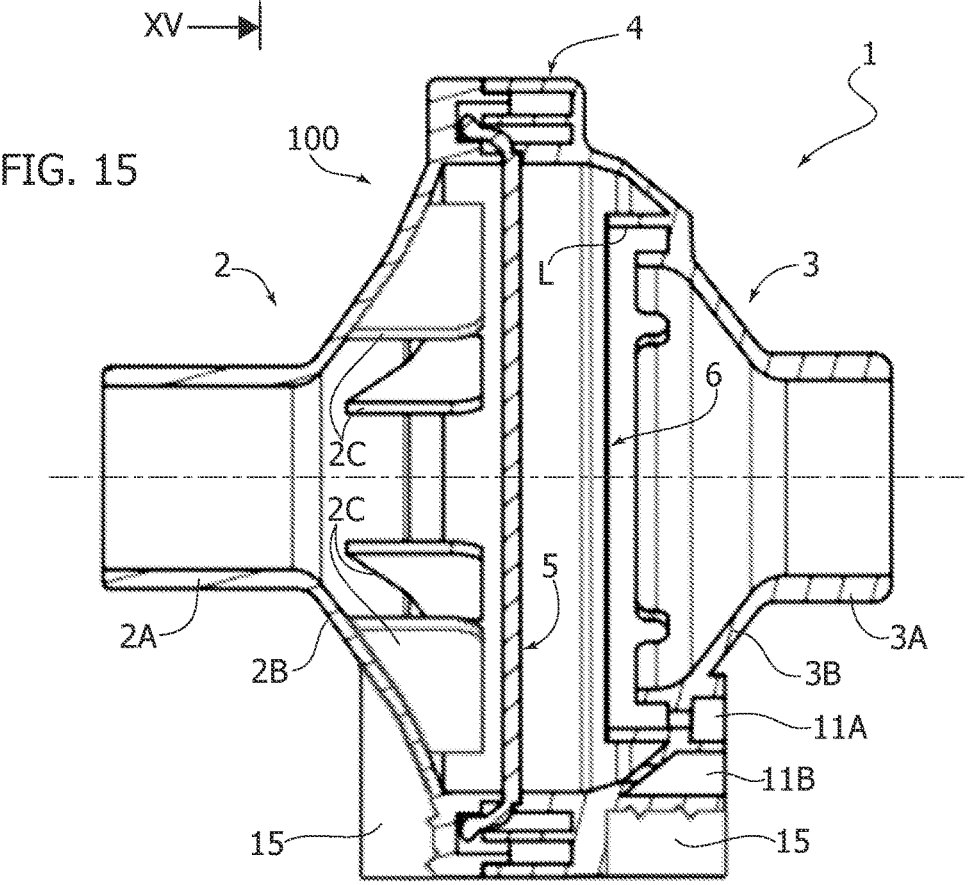

Further characteristics and advantages of the invention will become apparent from the description that follows with reference to the attached drawings, provided purely by way of non-limiting example, wherein:

FIG. 1 shows a known solution wherein an antimicrobial filter device and a flowmeter device constitute two separate elements, which are assembled together, and wherein only the filter device is of the disposable type, FIG. 2 is a side view of a first embodiment of a combined filter and flowmeter device, entirely disposable, according to the present invention, FIG. 3 is an exploded side view of the device of FIG. 2, FIG. 4 is a cross-sectional view of the device of FIG. 2, FIG. 5 is a variant of FIG. 4, which illustrates an example not forming part of the present invention FIGS. 6A and 6B are front views illustrating the pressure differential generator element of the example of FIG. 5, in two different operating conditions, FIG. 7 is a front view of the pressure differential generating network used in the embodiment of the present invention, which is illustrated in FIGS. 2-4, FIG. 8 is a side view of a preferred embodiment of a combined filter and flowmeter device, disposable, according to the present invention, FIG. 9 is an end view of the device of FIG. 8, FIG. 10 is a cross-sectional view along the line X-X of FIG. 9, FIG. 11 illustrates a detail of FIG. 10 on an enlarged scale, FIG. 12 is a perspective view of one of the bell-shaped half-shells of the device of FIG. 8, showing the radial fins formed on the inner surface of this component, FIG. 13 is a side view of another preferred embodiment of a combined filter and flowmeter device, disposable, according to the present invention, FIG. 14 is an end view of the device of FIG. 13, and FIG. 15 is a cross-sectional view along the line XV-XV of FIG. 14, FIG. 1 relates to the prior art and has already been described at the beginning of this description.

In FIG. 2, numeral 1 indicates—in its entirety—a combined filter and flowmeter device, entirely disposable, which can be used to carry out spirometry analyzes in order to evaluate the respiratory function of a user. A "disposable device" means a device intended to be used only once by a single user.

In the illustrated example, the device comprises a tubular body 1, which defines a passage for the airflow. The tubular body 1 comprises an inlet end portion 2A, for engaging the user's mouth, an outlet end portion 3A and an intermediate portion 100, shaped like a discoidal shell, having an enlarged diameter with respect to both the inlet and outlet end portions 2A, 3A (the terms "inlet" and "outlet" are used here with reference to the direction of airflow in an exhalation phase of the patient).

The inlet end portion 2A has a cylindrical shape, or alternatively an oval shape, like a mouthpiece, for greater user comfort. The outlet end portion 3A preferably has a cylindrical shape. The ratio between the outer diameter of the discoidal shell 100 and the largest dimension of the section of each of the two end portions 2A and 3A is at least equal to 2 and preferably is at least equal to 2.5.

In all the examples illustrated in the attached drawings, the discoidal shell 100 has an outer cylindrical wall 4 and two opposite bell-shaped portions 2B, 3B, which connect the cylindrical wall 4 with the end portions 2A, 3A.

In all the examples illustrated in the attached drawings, the body 1 of the device comprises a first element of plastic material 2, which includes, in one piece, the inlet end portion 2A and the bell portion 2B, and a second element of plastic material 3, which includes, in one piece, the outlet end portion 3A and the bell-shaped portion 3B Only in the example of FIGS. 2-4, the outer cylindrical wall 4 is defined by two additional cylindrical annular elements of plastic material 4A, 4B (see in particular FIG. 4), interposed between the outer peripheral edges of the two bell-shaped portions 2B, 3B and fitted in an annular seat 10 of the element 4B. The aforesaid elements of plastic material 4A, 4B are rigidly connected to each other and to the two elements 2, 3, for example, by means of adhesive and/or ultrasonic welding, or with any other prior art suitable for the object.

In all the examples illustrated in the attached drawings, both an antimicrobial filtering membrane 5 and a pressure differential generator member 6, in the form of a network of plastic material, are arranged inside the discoidal shell 100.

According to a per se known technique, the filtering membrane 5 comprises antimicrobial material, preferably antibacterial and/or antiviral material, and is preferably an electrostatic membrane, where "electrostatic membrane" means a membrane comprising a polymeric mixture capable of inducing the formation of a stable electric charge on the membrane itself.

The filtering membrane 5 is in the form of a substantially circular disc having a thickness preferably between 1 and 5 millimeters. It is to be understood that the filtering membrane 5 may be of a different shape from that represented, for example, it can have an elliptical, square, rectangular or triangular shape In general, the filtering membrane 5 may have any shape suitable for insertion into the discoidal shell 100 of the body 1 of the device.

As already indicated, according to the present invention, the pressure differential generator member is a network 6 of plastic material arranged inside the discoidal shell 100 together with the filtering membrane 5 and parallel and spaced apart with respect to the filtering membrane 5.

It should be understood that the expression "pressure differential generator member" as used herein refers to a member configured in such a way as to generate, following the passage of a flow of air through it, a pressure differential between the two sides upstream and downstream of the member.

In the illustrated examples, the network 6 for generating the pressure differential is in the form of a substantially circular disc.

In the embodiment illustrated in FIG. 4, the network 6 (of which FIG. 7 illustrates a front view) has an outer peripheral edge clamped between the two cylindrical annular elements 4A, 4B, in particular at the circumferential seat 10 of the annular element 4B. Again in the case of this embodiment, the filtering membrane 5 is a circular disc with an outer peripheral edge rigidly connected (for example, by adhesive or by welding, for example, ultrasonic welding) to an annular lip L, coaxial with the cylindrical wall 4 and protruding from the inner surface of the bell-shaped element 2B.

It is understood that both embodiments wherein the network 6 is entirely formed by meshes, and embodiments wherein the network 6 is only partially formed by meshes, fall under the scope of protection defined by the present description and, therefore, also includes portions wherein the surface is continuous and not perforated.

FIG. 5 illustrates an embodiment not forming part of the invention, wherein the pressure differential generator member is a membrane 7, having a thickness preferably less than 5 millimeters and configured with an orifice 8 whose opening is controlled by a flexible fin 9. In particular, the flexible fin 9 is designed to be deformed by the passage of the airflow, thus passing from a first operating condition wherein it is completely extended on the orifice 8, visible in FIG. 6A, to a second operating condition wherein it is raised so as to leave the orifice 8, visible in FIG. 6B, at least partially open. In the embodiment illustrated in FIGS. 5 and 6A-6B, the membrane 7 comprises a single orifice 8. However, the membrane 7 may comprise more than one single orifice 8. Preferably, the membrane 7 is of biocompatible plastic and/or steel. In the embodiment shown in FIGS. 6A-6B, the flexible fin 9 is connected at one end 9A to a portion of the edge of the orifice 8 formed in the membrane 7. However, it is to be understood that the flexible fin 9 may also be formed in one piece with the membrane 7.

In all the illustrated examples, a single filtering membrane 5 and a single pressure differential generating network 6 are inserted inside the discoidal shell 100. However, it is to be understood that embodiments also fall within the present invention wherein more than one filtering membrane 5 and/or more than one network 6 are arranged inside the discoidal shell of the device.

In all the illustrated examples, the tubular body 1 has two outlets 11A, 11B communicating, respectively, with two chambers 13A, 13B defined in the cavity of the body 1, respectively, upstream and downstream of the network 6 for generating the pressure differential.

In all the examples illustrated, the two outlets 11A, 11B are intended to be connected, for example, by means of flexible tubes 12 (see FIG. 4) with a measuring instrument of any known type (which does not form part of the present invention) capable of detecting the flow rate of the airflow passing through the device based on a measurement of the aforesaid pressure differential.

During use of all the embodiments described here, a user whose respiratory function is to be assessed by means of a spirometry analysis places his mouth around the inlet end portion 2A of the device. On the advice of a healthcare professional, the user performs one or more inhalations and/or exhalations of air. In the case wherein the user exhales, the exhaled air passes from the inlet end portion 2A to the discoidal shell 100, and then reaches the outlet end portion 3A, and is expelled into the external environment, following the path exemplified by the arrows in FIGS. 4-5. When the air passes through the discoidal shell 100, it first passes through the filtering membrane 5, and then through the network 6, thus generating a pressure drop whose measurement is indicative of the flow rate of the exhaled air. The passage through the filtering membrane 5, which comprises antimicrobial material, prevents the leakage of microbes into the external environment, for example, bacteria and/or viruses, which are possibly exhaled by the user, thus protecting the external environment and healthcare personnel from exposure to these microbes. Conversely, in the event that the user performs an inhalation, the air inhaled from the external environment passes into the outlet portion 3A and from there it passes into the discoidal shell 100, and then reaches the inlet portion 2A and is thus inhaled by the user, thus following a path that is the reverse of that illustrated by the arrows in FIGS. 4-5. When the air passes through the central portion 4, it first passes through the network 6, thus generating the pressure differential indicative of the flow rate of the inhaled airflow, and then through the filtering membrane 5. In this way, the filtering membrane 5 prevents the user from inhaling any microbes coming from the external environment.

In the embodiment of FIG. 5, which does not form part of the invention, the pressure differential generator member is a membrane 7 with an orifice 8 whose opening is controlled by a flexible fin 9. Before the passage of the airflow, the flexible fin 9 is not deformed and therefore completely covers the orifice 8, which is, therefore, substantially closed (FIG. 6A). As the airflow passes, the flexible fin 9 is stressed and deforms, flexing proportionally to the flow rate. The deformation of the fin 9 causes an opening of the orifice 8, so that the air passes therethrough, and a pressure difference is generated between the two sides upstream and downstream of the membrane 7, due to the pressure drop to which the airflow is subjected to.

FIGS. 8-12 and 13-15 illustrate two preferred embodiments of the present invention. In these figures, the parts common or corresponding to those of FIGS. 2-7 are indicated by the same reference numbers. In the case of both these embodiments, the body 1 of the device consists solely of the two elements of plastic material 2, 3. The elements 2, 3 have their respective bell-shaped portions 2B, 3B which have their outer peripheral edges directly connected to each other, for example by adhesive and/or by welding, for example, ultrasonic welding, in such a way as to define the outer peripheral wall of the discoidal shell 100.

In the embodiment of FIGS. 8-12, the network 6 constituting the pressure differential generator member is a circular disc with a peripheral edge clamped between the two outer peripheral edges of the two bell-shaped portions 2B, 3B.

FIG. 11 shows the detail on an enlarged scale of an embodiment example of the outer peripheral edges of the bell-shaped portions 2B, 3B. These outer circumferential edges define the outer cylindrical wall 4 of the discoidal shell 100 and have a series of annular lips 201, 202 and 301, 302, 303 in mutual engagement to define a labyrinth seal in which the outer peripheral edge of the network 6 is clamped. The filtering membrane 5, on the other hand, is rigidly connected, for example, by adhesive or by welding, to the circumferential lip L which protrudes from the inner surface of the bell-shaped portion 2B.

Still with reference to the embodiment of FIGS. 8-12, the bell-shaped portion 2B is conical in shape, with a radially inner portion having a lower inclination with respect to the axis X-X of the device (FIG. 10), and a radially outermost portion having a greater inclination angle, preferably between 50° and 90°.

Again with reference to the embodiment of FIGS. 8-12, the bell-shaped portion 3B has a conical shape with a single inclination, preferably between 50° and 90°, with respect to the axis X-X. In the case of this embodiment, moreover, the outlet end portion 3A has a larger diameter than the inlet end portion 2A. As already indicated, the inlet end portion 2A preferably has an oval configuration (not illustrated), like a mouthpiece, for a more comfortable engagement by the user's mouth.

With reference in particular to FIGS. 10 and 12, the inner surface of the bell-shaped portion 2B is provided with radial fins 2C to guide the flow inside the device, avoiding turbulence.

The radial fins 2C are also configured in such a way as to keep the filtering membrane in position, preventing it from inspiratory inflecting, due to an inhalation effect.

Again with reference to FIG. 10, in this example, the bell-shaped portion 3B is also provided on its inner surface with an annular lip L1, coaxial with the outer cylindrical wall 4 of the device, which has the object of limiting communication with the passage 11B.

Again with reference to the embodiment of FIGS. 8-12, the two outlet passages 11A, 11B are respectively defined in the bell-shaped portions 2B and 3B and include tubular fittings 14A, 14B projecting from opposite sides, in a direction parallel to the axis X-X of the device, from the two bell-shaped portions 2B, 3B.

The embodiment of FIGS. 13-15 differs from that of FIGS. 8-12 mainly due to the fact that—in this case—the outer peripheral edge of the filtering membrane 5 is clamped between the two outer circumferential edges of the bell-shaped portions 2B, 3B, while the pressure differential generating network 6 is rigidly connected (for example, by ultrasonic welding) to a circumferential lip L obtained on the inner surface of the bell-shaped portion 3B. In this case, the two outlets 11A, 11B are both formed in the bell-shaped portion 3B and extend through a longitudinal flattened fin 15, defined by the body of the device and protruding from the outer surface of the discoidal shell.

In all the embodiment examples described above, the predisposition, as a pressure differential generator member, of a network of plastic material, inserted into the discoidal portion 100 wherein the filtering membrane 5 is also inserted, allows obtainment of an adequate but not excessive resistance to flow, and a simple and reliable detection to be made possible, due to the fact that the pressure differential generated by the network 6 varies substantially linearly as the flow varies. Furthermore, the inner volume of the device and the dead space inside the device are reduced to a minimum.

Thanks to the volume reduction, the flow of inhaled/exhaled air by the user makes a relatively short path and, consequently, the risk of unwanted air leaks that could negatively affect the reliability of the measurement is considerably reduced. In addition to this, the dead space, i.e. the volume of air that remains trapped in the device and which is consequently breathed in again by the user during the analysis, is also significantly reduced.

The combined antimicrobial filter and flowmeter device according to the present invention, being entirely disposable, allows healthcare personnel to operate safely and to reduce the risk of coming into contact with the user's viruses and/or bacteria.

Tests and studies carried out by the Applicant have led to identifying the need for the network of plastic material 6 constituting the pressure differential generator member to have a resistance to the airflow that is neither too high nor too low. Preferably, the permeability to the airflow of the network 6 must be between 3000 liters/sec m$^2$ and 6600 liters/sec m$^2$.

Of course, without prejudice to the principle of the invention, the details of construction and the embodiments may vary widely with respect to those described and illustrated purely by way of example, without departing from the scope of protection of the present invention, as defined by the attached claims.

What is claimed is:
1. A combined antimicrobial filter and flowmeter device, entirely disposable, the device comprising:
 a tubular body, defining a cavity for the passage of an airflow, the tubular body having
  an inlet end portion configured to engage the mouth of a user,
  an opposite outlet end portion that is substantially coaxial with the inlet end portion, and
  an intermediate portion having an enlarged diameter with respect to the inlet end portion and the outlet end portion;

a filtering membrane disposed inside said intermediate portion of enlarged diameter, to filter the entire airflow that passes through said tubular body;

a pressure differential generator member that is a membrane parallel to and spaced apart from said filtering membrane, inside said intermediate portion of enlarged diameter, said pressure differential generator member being configured to generate a pressure differential, in the entire airflow that passes through said tubular body, between an upstream side and a downstream side of said pressure differential generator member, with reference to the direction of the airflow; and two outlets defined by said tubular body and communicating, respectively, with two chambers defined in the cavity of said tubular body, respectively, upstream and downstream of said pressure differential generator member, wherein said intermediate portion of enlarged diameter is a discoidal shell comprising an outer cylindrical wall and two opposed bell-shaped portions, connecting the outer cylindrical wall, respectively, with the two inlet and outlet end portions of said tubular body, said membrane defining said pressure differential generator member is a discoidal pressure differential generating network of plastic material and is located, together with said filtering membrane, inside said discoidal shell of enlarged diameter, the tubular body comprises
- a first element of plastic material comprising, in one piece, the inlet end portion and one of the conical bell-shaped portions, and
- a second element of plastic material comprising, in one piece, the outlet end portion and the other of the conical bell-shaped portions, said filtering membrane has an outer peripheral edge fixed to said cylindrical wall of the discoidal shell, while said pressure differential generating network has an outer peripheral edge fixed to an inner annular lip of the other bell-shaped portion of the discoidal shell, the inner annular lip extending into the cavity from an inner surface of the other bell-shaped portion, inner annular lip being coaxial to said cylindrical wall.

2. The device according to claim 1, wherein said network of plastic material is configured to have an air permeability of between 3000 liters/second $m^2$ and 6600 liters/second $m^2$.

3. The device according to claim 1, wherein said first element of plastic material and said second element of plastic material have radially outer edges directly connected to each other, to define said cylindrical wall, one of said filtering membrane and said pressure differential generating network having its outer peripheral edge clamped between said radially outer edges of the first and second elements of plastic material.

4. The device according to claim 3, wherein:
said filtering membrane has the peripheral outer edge clamped between said radially outer edges of the first and second elements of plastic material,
said network generating a pressure differential has its outer peripheral edge fixed to said inner annular lip, said lip being formed in the bell-shaped portion of said second element of plastic material, which comprises said outlet end portion, and
both said outlet passages are formed in the bell-shaped portion of said second element of plastic material, which comprises the outlet end portion, an outlet passage being in communication with a chamber defined between the filtering membrane and the pressure differential generating network, the other outlet passage being in communication with a chamber located downstream of the pressure differential generating network.

5. The device according to claim 1, wherein said filtering membrane is an electrostatic membrane.

6. The device according to claim 4, wherein each of said outlets comprises an outer end portion oriented parallel to the axis of said tubular body.

7. The device according to claim 1, wherein the one bell-shaped portion is conical with a radially inner portion having a lower inclination angle with respect to the longitudinal axis of the device than an inclination angle of a radially outermost portion of the one bell-shaped portion.

8. The device according to claim 7, wherein the inclination angle of the radially outermost portion is between 50° and 90°.

* * * * *